United States Patent [19]

Livingston

[11] Patent Number: 4,853,373

[45] Date of Patent: Aug. 1, 1989

[54] THERAPEUTIC TREATMENT FOR ARTHRITIC CONDITION

[76] Inventor: William S. Livingston, 1080 Triunfo Canyon Rd., West Lake Village, Calif. 91361

[21] Appl. No.: 907,623

[22] Filed: Sep. 15, 1986

[51] Int. Cl.$^4$ .................. A61K 31/52; C07H 19/16
[52] U.S. Cl. .................. 514/46; 514/262; 536/24; 536/26; 544/265
[58] Field of Search .................. 514/46, 262; 536/24, 536/26; 544/265

[56] References Cited

U.S. PATENT DOCUMENTS

| | | | |
|---|---|---|---|
| 3,208,997 | 9/1965 | Iwai et al. | 536/26 |
| 4,021,556 | 5/1977 | Springer et al. | 424/251 |
| 4,091,097 | 5/1978 | Umezawa et al. | 424/230 |
| 4,256,887 | 3/1981 | Novello et al. | 544/333 |
| 4,309,419 | 1/1983 | Wolberg et al. | 536/24 |
| 4,322,411 | 3/1982 | Vinegar et al. | 536/24 |
| 4,335,040 | 6/1982 | Livingston | 530/427 |
| 4,544,752 | 10/1985 | Beck et al. | 548/214 |

FOREIGN PATENT DOCUMENTS

| | | | |
|---|---|---|---|
| 3319282 | 11/1984 | Fed. Rep. of Germany | 514/46 |
| 2010136 | 6/1969 | France | 514/262 |
| 48-28438 | 9/1973 | Japan | 536/24 |
| 1075008 | 7/1967 | United Kingdom | 544/265 |

OTHER PUBLICATIONS

Tietz, Fundamentals of Clinical Chemistry, pp. 27–30, W. B. Saunders Company, 1970.
Strong et al., The Biological Abstracts, 60250, 65, May 1978.
Merck Index, Tenth Edition, p. 4792.
Naruse, The Biological Abstracts, 64396, 64 (1977).
Controlled Study of a New Antiarthritic Substance, by T. Reed Maxson, MD., F.A.C.A. and Edgar L. Compton, M.D., F.A.C.A. (Feb. 1969).
Growth Inhibition of Transplantable Mouse Lymphosarcoma by a Filtrate from Placental Lysates by W. Steele Livingston, D.V.M. and Baldwin G. Lamson, M.D. (May 8, 1969).
The Treatment of Spontaneous Tumors of the Dog and Cat with a Filtrate from a Tissue Lysate, by W. Steele Livingston, D.V.M. (Feb. 1952).
The Livingston Placental Autolysate, by W. Steele Livingston, D.V.M., and Edgar L. Compton, M.D. (Oct. 1967).

Primary Examiner—Joseph L. Schofer
Assistant Examiner—Gary L. Kunz
Attorney, Agent, or Firm—Hale and Dorr

[57] ABSTRACT

Hypoxanthine administered intradermally at a dosage range of $2 \times 10^{-8}$ to $1 \times 10^{-5}$ grams to a mammalian subject for the purpose of treating rheumatoid arthritis and osteoarthritis.

2 Claims, No Drawings

THERAPEUTIC TREATMENT FOR ARTHRITIC CONDITION

FIELD OF THE INVENTION

This invention relates to the treatment of arthritis and, more particularly, to such treatment by intradermal administration of low doses of hypoxanthine.

BACKGROUND OF THE INVENTION

U.S. Pat. Nos. 3,526,697 and 4,335,040 disclose producing a therapeutic product by a process of autolysis of animal tissue in which a quantity of material comprising animal tissue is placed in a pressure vessel, the vessel is enclosed, sealed, and maintained at a temperature in the range of about 5 to about 65 degrees centigrade and a pressure in the range of about 15 to 45 psig for a period of not less than about two weeks, and the liquid portion of the semi-liquid thereby produced is recovered and sterilized. As discussed in such patents, the material thus produced is useful in the treatment of rheumatoid arthritis and osteoarthritis. The patents state that treatment is by intravenous or intercutaceous injection, preferably intercutaceous, and that mice have been treated intraperitonically.

Livingston Placental Autolyste (LPA) is a complex mixture of substances derived from the autolysis of human placentae under the conditions defined in the patents, and in the California veterinarian industry is known as Scott A-510. The use of LPA in the treatment of tumors and arthritis has been reported in e.g., Livingston, W.S., "The Treatment of Spontaneous Tumors of the Dog and Cat With a Filtrate From a Tissue Lysate", J. Nat. Cancer Inst., 1958, 20:245-306; Livingston, W.S., "Growth Inhibition of Transplantable Mouse Lyphosarcoma by a Filtrate from Placental Lysate", J. Nat. Cancer Inst., 1959, 23:597-603; Bender, W. M. "Nontraditional Treatment of Mycosis Fungoides in a Dog", J. Am. Vet. Med. Assn. 1984, 185:900-901; and Maxson, T. R. and Compton, E.L., "Controlled Study of a New Anti-Arthritic Substance", Ann. Allergy, 1969, 21:54-64.

SUMMARY OF THE INVENTION

It has now been discovered that the complex mixture of substances in LPA, i.e., in products made from human placentae according to the procedure described in the aforementioned patents, includes hypoxanthine. It has been discovered also that hypoxanthine is effective in treating arthritis if administered intradermally at low (e.g., not more than about 0.1 mg., and preferably less than about 0.001 mg., of hypoxanthine) dose.

A first aspect of the invention accordingly features the method of treating a human or other mammalian arthritic subject by intradermal administration of a low dose of hypoxanthine, and a second aspect features the method of such treatment which comprises the administration, intradermal or otherwise, of a low doses of hypoxanthine that has been produced other than by autolysis, i.e., by a method other than that disclosed in the aforementioned patents. In preferred practices, which encompass both aspects, the dose level is not more than about 0.001 mg. active material (e.g., 0.1 cc dose of a dilution not stronger than about 1 mg. of active material per 100 cc of diluent), the dose is injected intradermally.

DETAILED DESCRIPTION

Sigma grade hypoxanthine, and the bases of RNA and DNA and the glucosides of the bases, were obtained from Sigma Chemical Co. of St. Louis, Missouri. Using these materials, a number of tests were conducted.

In each test, the active material to be administered was dissolved in a normal physiological saline solution (e.g., 100 mg. of hypoxanthine was dissolved in 100 cc of saline to produce a "1:10" dilution). This dilution was then further adjusted (if required) to insure that a 0.1 cc dose would include the desired quantity of the active material. The resulting active materialsaline dilution was injected intradermally, preferably just below the squamous layer.

In conducting tests with hypoxanthine, the initial 1:10 dilution of 100 mg hypoxanthine in 1000 cc of normal physiological saline solution was produced at a temperature of about 55°-65° centigrade (to which gentomycin was added as a preservative), at which temperature that quantity of hypoxanthine could be dissolved in the saline solution. At room or body temperature, about 1400 cc of saline solution is required to dissolve 100 mg of hypoxanthine. The 1:10 dilution was then further diluted by adding additional saline solution (and typically adding 0.9% benzyl alcohol as a preservative also).

Hypoxanthine has been found to be effective in treating arthritis. In treating both dogs and humans, an 0.1 cc dose of the desired dilution is administered intradermally, preferably by injection, once a day.

In dogs, intradermal injection of 0.1 cc doses of 1:500 dilution (e.g. 100 mg. of hypoxanthine dissolved in 50,000 cc of saline) have generally proved the most effective; but 0.1 cc doses of dilutions as concentrated as 1:10 (0.01 mg. active material per dose) or as dilute as 1:5,000 ($2 \times 10^{-4}$ mg. active material per dose) have in some animals, also been found effective.

Rheumatoid arthritis has proved to be especially sensitive to treatment with hypoxanthine, and improvement in humans has resulted from intradermal injection of doses as dilute as 1:100,000 or 1:200,000. In human arthritic patients generally, however, doses of dilutions of about 1:500 have proved to be the most effective. Typically, the desired concentration for a particular human subject is determined by starting with an initial dose of a 1:200,000 dilution of hypoxanthine in normal saline, and the concentration of the dose then is increased by increments (e.g., 1:100,000, 1:10,000, 1:1000, 1:100, etc.) until the patient shows improvements, at which time the level is maintained. In arthritic patients, the dose concentration is decreased slightly if the subject experiences increased pain which subsides before the next injection is due. This method of determining the desired effective dose for a particular patient is similar to that used in the treatment of allergies with antigen.

It is apparent that the low doses of hypoxanthine which are the subject of the present invention may be intradermally administred in a number of ways other than intradermal injection. Two other methods of intradermal administration which would result in the desired delivery of the active material to within the skin, for example to the keratin tissue of the epidermis, are skin patches and trans-dermal carriers.

These and other embodiments will be within the scope of the following claims.

What is claimed is:

1. A method for the treatment of mammalian rheumatoid arthritis and osteoarthritis comprising intradermal administration of hypoxanthine of at least 95% purity in a dosage range of $2 \times 10^{-8}$ to $1 \times 10^{-5}$ grams to a mammal in need of said treatment.

2. The method of claim 1 where said hypoxanthine dosage is administered in a total volume of 0.1 cc.

The title of the invention is not descriptive. A new title is required that is clearly indicative of the invention to which the claims are directed.

* * * * *

UNITED STATES PATENT AND TRADEMARK OFFICE
CERTIFICATE OF CORRECTION

PATENT NO. : 4,853,373

DATED : August 1, 1989

INVENTOR(S) : William S. Livingston

It is certified that error appears in the above-identified patent and that said Letters Patent is hereby corrected as shown below:

In column 1, line 60, delete "doses" and substitute --dose--;

In column 2, line 10, delete "100" and substitute --1,000--;

In column 2, line 14, delete "materialsaline" and substitute --material-saline--;

In column 2, line 50, delete "improvements" and substitute --improvement--;

In column 4, lines 3-5 are inappropriate and should be deleted.

Signed and Sealed this

Eighteenth Day of February, 1992

Attest:

HARRY F. MANBECK, JR.

Attesting Officer

Commissioner of Patents and Trademarks